(12) United States Patent
Ottoboni et al.

(10) Patent No.: US 10,010,349 B2
(45) Date of Patent: Jul. 3, 2018

(54) ELONGATED PIN FOR APPLICATION OF AN EXTERNAL FIXATOR

(71) Applicant: ORTHOFIX S.R.L., Verona (IT)

(72) Inventors: Andrea Ottoboni, Rovigo (IT); Daniele Venturini, Verona (IT)

(73) Assignee: Orthofix S.R.L., Verona (IT)

( * ) Notice: Subject to any disclaimer, the term of this patent is extended or adjusted under 35 U.S.C. 154(b) by 0 days.

(21) Appl. No.: 15/543,939

(22) PCT Filed: Dec. 21, 2015

(86) PCT No.: PCT/EP2015/080734
§ 371 (c)(1),
(2) Date: Jul. 14, 2017

(87) PCT Pub. No.: WO2016/116237
PCT Pub. Date: Jul. 28, 2016

(65) Prior Publication Data
US 2018/0008316 A1    Jan. 11, 2018

(30) Foreign Application Priority Data
Jan. 19, 2015 (EP) .................................... 15425003

(51) Int. Cl.
*A61B 17/00* (2006.01)
*A61F 4/00* (2006.01)
(Continued)

(52) U.S. Cl.
CPC ........ *A61B 17/6458* (2013.01); *A61B 17/861* (2013.01); *A61B 17/8635* (2013.01)

(58) Field of Classification Search
CPC .......... A61B 17/58; A61B 17/60; A61B 17/62
(Continued)

(56) References Cited

U.S. PATENT DOCUMENTS

2014/0031822 A1* 1/2014 Venturini ............... A61B 17/64
606/59

FOREIGN PATENT DOCUMENTS

WO    2015110266 A1    7/2015

OTHER PUBLICATIONS

International Search Report dated Apr. 8, 2016 in connection with International Application No. PCT/EP2015/080734, 3 pages.
(Continued)

*Primary Examiner* — Ellen C Hammond
*Assistant Examiner* — Christina Negrellirodrigue
(74) *Attorney, Agent, or Firm* — Baker & McKenzie LLP

(57) ABSTRACT

Monocortical pin (1) for an external fixator for temporary and/or permanent fixing applications for treating bone fractures and connecting two or more bone fragments together, comprising an elongated cylindrical stem (2) which extends along a longitudinal axis (X) and a conical portion (3) with a tip having an external thread for inserting the pin (1) inside a bone; where said elongated cylindrical stem (2) has a flattened surface (2a) which lies along a reference plane (A) parallel to the longitudinal axis (X) and said conical portion (3) with the tip has an overall length, measured along the longitudinal axis, equal to the diameter (d) of the stem (2) +20% of said diameter (d); said monocortical pin (1) is characterized in that the conical portion (3) comprises a tip (31) which has a centring zone (33) which extends longitudinally over a length equal to 6-8% of the diameter (d) of the stem (2), and a threaded portion (32); moreover the conical portion (3) comprises two base cones (3a and 3b) having two different angles of conicity, a first base cone (3a) in a distal position with respect to the elongated cylindrical stem (2) of the monocortical pin and a second base cone (3b) in a proximal position with respect to the elongated cylindrical stem (2) of the monocortical pin; said first base cone (3a)

(Continued)

having an angle of conicity of 13°; said second base cone (3*b*) having an angle of conicity of 26°.

9 Claims, 3 Drawing Sheets

(51) Int. Cl.
    *A61F 5/04*     (2006.01)
    *A61B 17/64*     (2006.01)
    *A61B 17/86*     (2006.01)

(58) Field of Classification Search
    USPC ................ 606/54, 59, 62–64, 300–321, 105
    See application file for complete search history.

(56) References Cited

OTHER PUBLICATIONS

Written Opinion of the International Searching Authority dated Apr. 8, 2016 in connection with International Application No. PCT/EP2015/080734, 5 pages.

\* cited by examiner

ELONGATED PIN FOR APPLICATION OF AN EXTERNAL FIXATOR

CROSS-REFERENCE TO RELATED APPLICATION(S)

The present application claims priority under 35 U.S.C. 365 to International Patent Application No. PCT/EP2015/080734 filed Dec. 21, 2015, entitled "ELONGATED PIN FOR APPLICATION OF AN EXTERNAL FIXATOR", and through International Patent Application No. PCT/EP2015/080734, to European Patent Application No. 15425003.9 filed Jan. 19, 2015, each of which are herein incorporated by reference in entirety.

TECHNICAL FIELD

The present invention relates to an elongated pin for an external fixator having the function of a monocortical pin.

PRIOR ART

External fixation systems are widely used to treat bone fractures and to connect two or more bone fragments together. Known systems use bone screws, screws and/or wires which are inserted inside the bones and which use external structural elements such as fixing clamps, fixing bars or annular bars to ensure a rigid structure which keeps the bone fragments stationary and therefore allows permanent healing by means of the external fixator or by means of internal stabilization systems such endomedullary plates or nails.

In some types of treatment, particular local conditions in the fracture zone may occasionally preclude the use of permanent fixators, or the fracture may be present along with other fractures due to an injury which requires fairly lengthy surgical treatment before a permanent internal fixation system may be used.

In these cases also, some or all the fractures may be treated with external fixation systems which are specifically designed for temporary fixing and which therefore may be regarded as temporary systems, as for example described in EP 2,319,436 in the name of the same Applicant.

In any case it is very important that, at the end of treatment, each fracture is contained in a stable manner.

In this technical sector there are also many fixing systems which are used mainly as permanent fixing systems for allowing bone fractures to heal, such as the system described in EP 1,284,666 in the name of the same Applicant.

In general the temporary fixing systems are lighter and simpler, but are also less stable compared to the known permanent external fixation systems. Moreover, temporary and permanent external fixation systems may often differ in terms of the form and structure of the respective clamps.

Still in general terms, permanent external fixation systems offer a high degree of rigidity and stability for managing the lateral flexural forces and twisting torque during treatment.

Such rigidity and stability are derived partly from the alignment of the bars of the fixator along the longitudinal axis of the bone which is treated, partly from the intrinsic rigidity of the system and partly from the number of screws used.

It would be highly desirable to have the possibility of using an external fixator which combines the characteristics of simplicity and lightness of a temporary fixing system and the robustness and stability characteristics of a permanent fixing system, which damages as little as possible the bone structure so as not to adversely affect the definitive internal or external stabilization, but hitherto all the methods known from the known solutions have not produced satisfactory results.

US 2014/0031822 discloses an elongated pin for an external fixator according to the prior art.

The technical problem of the present invention is that of providing an elongated pin for an external fixator which is able to ensure stable and robust fixing of the bone fragments and which affects as little as possible the bone structure in order to avoid subsequent infection and stabilization problems, while at the same time keeping the entire system extremely light and also ensuring easy application for the surgeon.

Another object of the present invention is to provide an elongated pin for a fixing system which may be inserted in the bone without the use of conventional bone screws, which allows the gripping action to be limited to the cortical portion alone of the fractured bone in the zone where there is a cortical bone of certain thickness and which at the same is able to ensure a good grip also in the spongy bone.

The present invention also improves the reliability and precision with which application is performed by the surgeon, limiting the possibility of damage occurring to the cortical portion of the fractured bone during insertion of the pin.

SUMMARY OF THE INVENTION

These objects are achieved by an elongated pin for an external fixator, in accordance with claim 1 of the present invention.

The dependent claims define preferred and particularly advantageous embodiments of the elongated pin according to the invention.

Further characteristic features and advantages will emerge more clearly from the detailed description provided hereinbelow of a preferred, but not exclusive embodiment of the present invention, with reference to the attached figures, provided by way of a non-limiting example.

DETAILED DESCRIPTION

Figure 4:
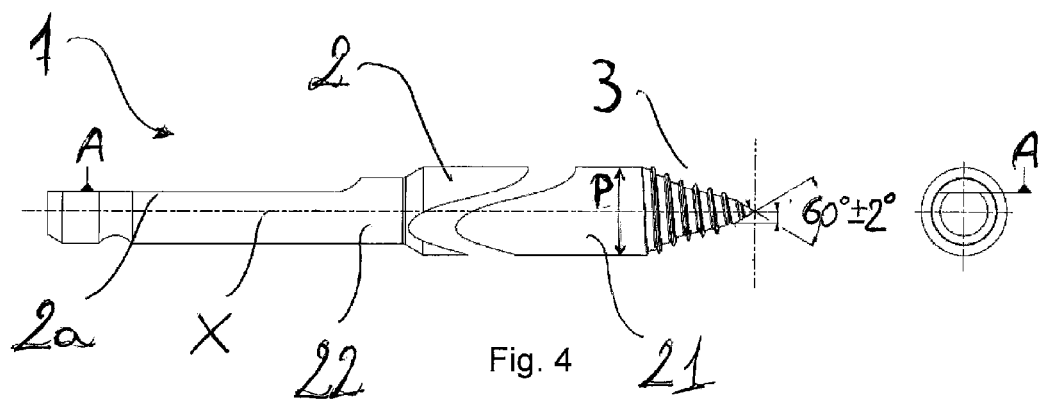
FIG. 4 shows a side view of the monocortical pin according to the present invention, positioned with the flattened surface situated at right angles relative to the plane of the sheet.
Figure 5:
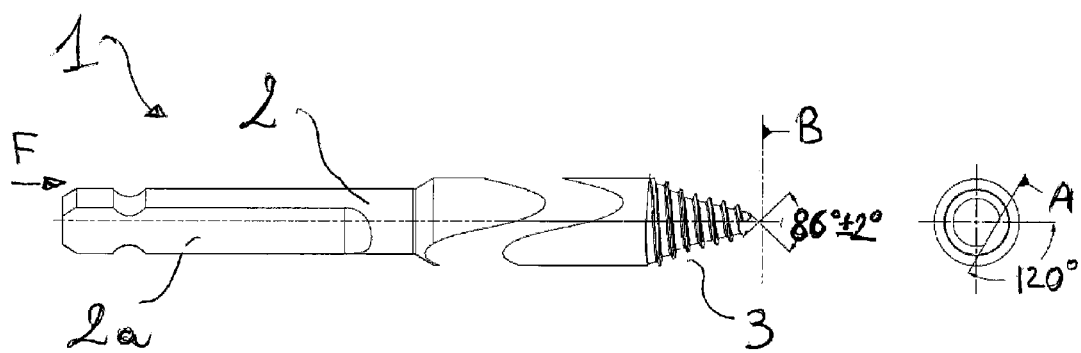
FIG. 5 shows a side view of the monocortical pin according to FIG. 4, positioned with the flattened surface rotated through 120° in the clockwise direction viewed in the direction of the arrow F.
Figure 6:
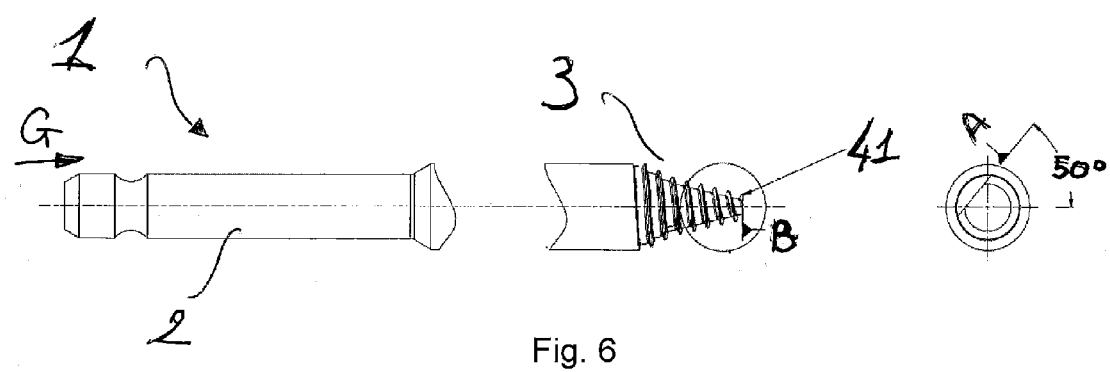
FIG. 6 shows a side view of the monocortical pin according to FIG. 4, positioned with the flattened surface rotated through 50° in the anti-clockwise direction viewed in the direction of the arrow G.

With reference to the attached FIGS. 4-6, the reference number 1 indicates overall an elongated pin comprising an elongated cylindrical stem 2 extending along a longitudinal axis X and a conical portion 3 with a tip having an external thread for inserting the pin 1 into a bone.

Below, the elements closest to the end of the pin facing the operator will be referred to as being proximal, while the elements situated furthest from the operator will be referred to as being distal.

The elongated cylindrical stem 2 comprises a first distal portion 21 with a diameter d and a second proximal portion 22 which has a flattened surface 2a for allowing fitting of a spanner or insertion of a drill so as to be able to drill the bone. Said flattened surface 2a lies along a plane parallel to the longitudinal axis X (FIG. 4).

Furthermore a reference plane A is defined, said plane corresponding to the plane along which said flattened surface 2a lies, relative to which the angular values of the elements of the monocortical pin described below will be determined. In particular, when said reference plane A lies in a horizontal position (viewed at right angles to the plane of the sheet), the angle of rotation of the pin about the longitudinal axis X is considered to be equal to 0° (FIG. 4).

Figure 1:
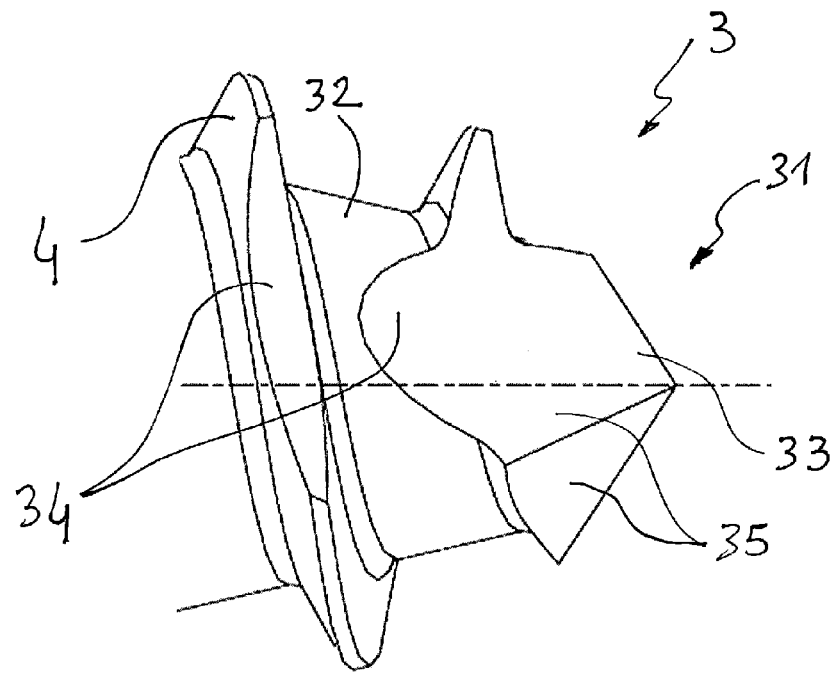
FIG. 1 shows a side view of the tip of the conical portion of a monocortical pin according to the present invention.

In accordance with the present invention the conical portion 3, which has an overall length, measured along the longitudinal axis X, equal to the diameter d of the stem ±20% of the diameter d itself, comprises a tip 31 and a threaded portion 32 (FIGS. 1 and 4).

It should be noted that threaded portion 32 occupies exclusively the conical portion 3, not extending onto the elongated cylindrical stem 2, and that the length of said conical portion 3 of the pin has a smaller length compared to conventional pins. Owing to these characteristics, the pin may be inserted in only the cortical portion of the bone without penetrating into the medullary cavity.

In other words, the elongated pin 1 may be defined as being a "monocortical pin".

Figure 2:
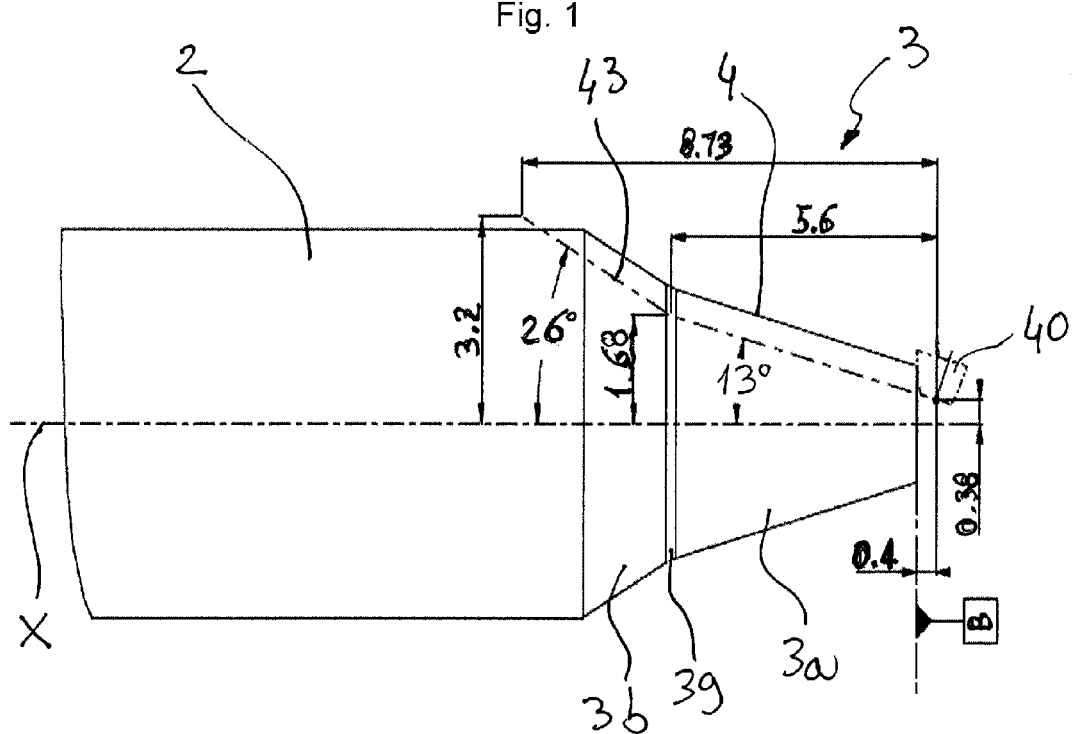
FIG. 2 shows a side view of the conical portion with a simplified illustration of the thread and a part of the elongated cylindrical stem of the monocortical pin according to the present invention.

In accordance with the present invention, the conical portion 3 comprises a first base cone 3a in a distal position with respect to the elongated cylindrical stem and a second base cone 3b in the proximal position. Said first base cone 3a (that closest to the tip) has an angle of conicity of 13°, while the second base cone 3b (that furthest from the tip) has an angle of conicity of 26°, as can be seen from FIG. 2.

In other words, on the conical portion 3 there is a change in the angle of conicity of the base cone and in particular doubling of this angle in the vicinity of the stem 2.

This change in conicity is provided in order to obtain a corresponding increase in torque which occurs close to the end of the insertion travel.

Therefore, for the same depth of insertion of the tip inside the bone, a firmer grip of the pin therein is ensured.

In order to achieve this, with reference again to FIG. 2, generally it is sufficient to provide a first base cone 3a (that closest to the tip) with a longitudinal extension approximately 1.8 times the longitudinal extension of the second base cone 3b (that furthest from the tip). Obviously the absolute dimensions of both the cones 3a and 3b will also vary depending on the dimensions of the pin.

It should also be noted that, in the region where said change in conicity occurs, a connecting zone 39 is provided (visible only in the enlarged view of FIG. 2), said connecting zone having a small extension on the lateral surface 43 of the conical portion.

This connecting zone allows the travel of a threading tool 40 to be varied during formation of the thread 4, without any interruptions in the machining.

Preferably the angle of the base cone and the travel path of the threading tool have a tolerance of +/−1°.

Preferably, the conical portion 3 has in the distal zone a cutting face 34 formed by means of removal of material from the pin.

More specifically, the cutting face 34 extends from the tip 31 over a distance, along the longitudinal axis X, equal to about 40% of the diameter d of the stem 2, and occupies the first section of the external thread 4.

As can be clearly seen in FIG. 1, the cutting face 34 removes a portion of the first two more distal threads of the cutting portion 3.

The tip of the conical portion 3 is created by means of inclined surfaces 35 which meet at an end point. This end point is the first element to make contact with the bone during insertion of the pin.

These inclined surfaces 35 form a centring zone 33 which extends longitudinally along the axis X over a distance equal to 6-8% of the diameter d of the stem 2 of the pin.

The presence of said centring zone 33 is necessary owing to the small dimensions of the conical portion 3 which do not allow the creation of a pre-hole for guiding the pin during threading of the bone. In this way instead a small conical guide point is created on the bone surface, this allowing stabilization, during the first cutting steps, of the position of the pin at the point chosen for insertion thereof.

This configuration moreover is such that rotation of the pin in the bone causes the bone to be cut.

In other words, the elongated pin 1 may be defined as being a "self-tapping pin".

The zone of the conical portion 3 which is occupied by the cutting face 34, although very short, performs both the drilling function and the screwing function. Moreover, with this configuration, the cutting face 34 also performs the role of a fluting in that it allows the evacuation of the bone material removed from the cutting zone.

Obviously, since the longitudinal extension of the cutting face 34 is very small, the evacuation of the bone material removed is performed only at the start of the screw insertion operation.

In accordance with a preferred embodiment of the present invention, below the geometrical characteristics of the tip 31 of the conical portion 3 will be described depending on the angles of rotation of the pin 1 (phases) relative to a reference position (0°) defined by the flattened surface 2a of the stem 2.

With reference to FIG. 4, in which the pin 1 is positioned laterally with respect to the plane of lie of the flattened surface 2a situated at right angles to the plane of the sheet, it can be seen that the tip 31 has an angle of conicity of 60° (with a tolerance of about +/−2°).

Similarly, in FIG. 5, in which the pin 1 is positioned laterally with the flattened surface 2a rotated through 120° in a clockwise direction viewed in the direction of the arrow F, it can be seen that the tip 31 has an angle of conicity of 86° (with a tolerance of about +/−2°).

With reference to FIG. 6, in which the pin is positioned laterally with the flattened surface rotated through 50° in an anti-clockwise direction viewed in the direction of the arrow G, the start of the thread formed by the first crest 41 of the more distal thread can be seen.

Basically, the inclined surfaces 35 present on the tip of the conical portion 3 and comprising the cutting face 34 are oriented so as to form different angles of conicity on said tip 31.

Owing to this configuration of the tip it is possible to remove more easily the hardest part (outer part of the cortex) of the bone for subsequent engagement of the thread 4, when the pin is inserted inside the bone.

Moreover, the angular position of said inclined surfaces 35 with respect to the helix of the external thread 4 is fundamental for ensuring correct engagement of the thread on the bone. Therefore, for these angular measurements a tolerance of +/−1° must be ensured.

Finally, in a further preferred embodiment according to the present invention, the threading 4 has an asymmetrical geometry, i.e. the two flanks of the crest 42 of said thread 4 have a different inclination.

Figure 3:
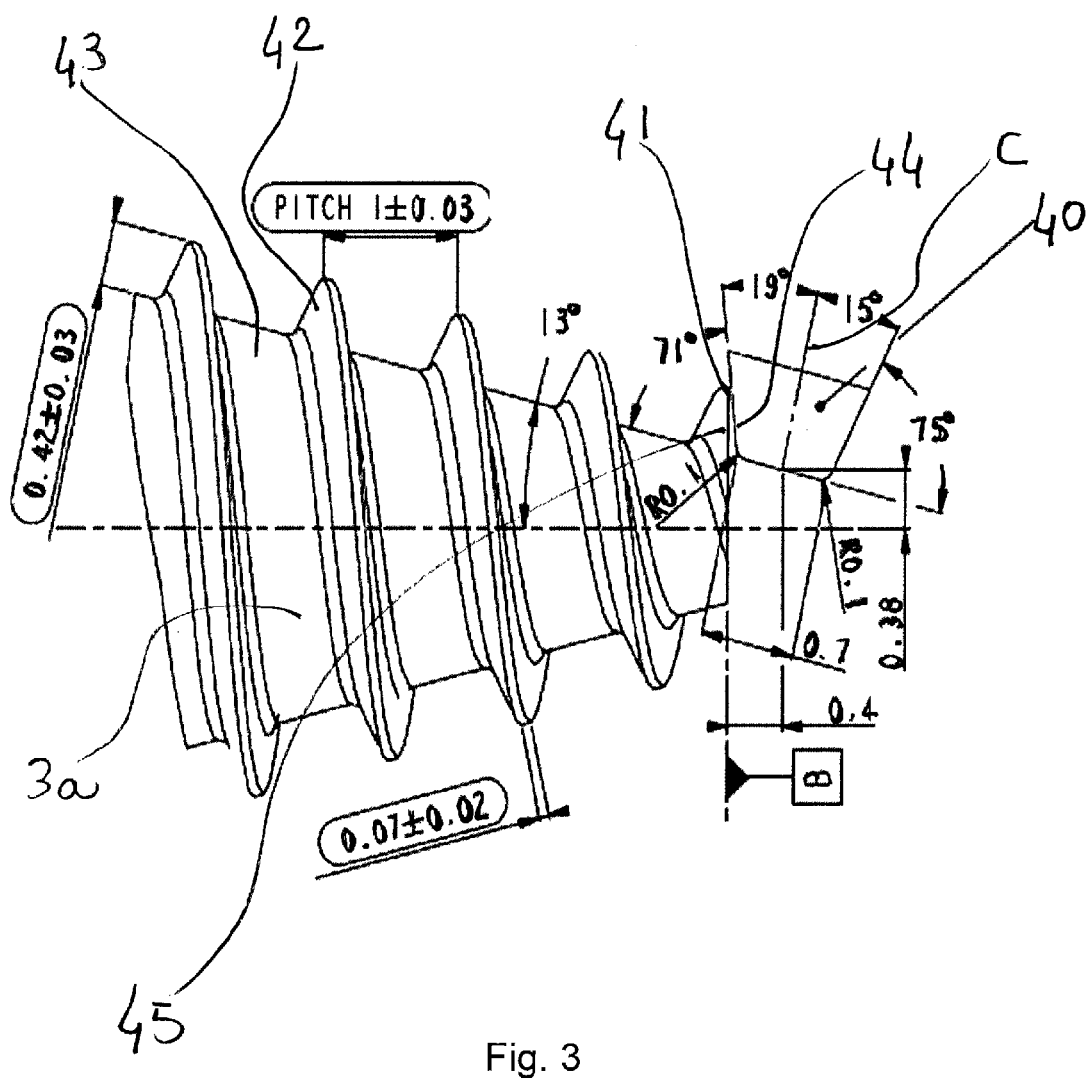
FIG. 3 shows a side view of the conical threaded portion of the monocortical pin of the present invention and a schematic illustration of the associated threading tool.

This different inclination is obtained by using a threading tool 40 also having an asymmetrical geometry, as shown in FIG. 3.

Still with reference to FIG. 3, the distal flank 44 of the thread is inclined by 19° while the proximal flank 45 is inclined by 15°. These inclination measurements are expressed with respect to a centre plane C located perpendicular to the lateral surface 43 of the base cone 3*a* and then rotated through an angle equal to the angle of conicity relative to the axis perpendicular to the longitudinal axis X.

The different inclination of the flanks of the thread is present along the entire conical portion and therefore both on the distal base cone 3*a* and on the proximal base cone 3*b*.

As a result of the geometry described it is possible to obtain a correct increase in torque during insertion of the pin into the bone and consequently a correct distribution of pressure over the cortex so as to prevent the formation of fissures therein.

In other words, the asymmetrical profile of the threading 4 reduces the possibility that damage to the cortical portion of the bone may occur during application of the monocortical pin.

The numerical values indicated in the attached figures are to be understood as being in millimeters.

With reference to the figures, these show, for example a pin, whose length is equal to 115 mm, the length of the conical end portion being equal to 7.8+/−0.5 mm, with a diameter d of the stem of 6 mm.

With regard to the change in conicity, the first base cone extends longitudinally over 5.2 mm. The external thread instead has crests with a height of 0.42+/−0.03 mm and spacing of 1+/−0.03 mm. The minimum thickness measured at the apex of the crest is equal to 0.07+/−0.02 mm.

As can be understood from the above description, the elongated pin according to the present invention is able to meet the requirements and overcome the drawbacks mentioned above in the introductory part of the present description with reference to the prior art.

Obviously a person skilled in the art, in order to satisfy any specific requirements which might arise, may make numerous modifications and variations to the invention described above, all of which are contained moreover within the scope of protection of the invention, as defined by the following claims.

The invention claimed is:

1. A monocortical pin for an external fixator for temporary and/or permanent fixing applications for treating bone fractures and connecting two or more bone fragments together, comprising an elongated cylindrical stem which extends along a longitudinal axis and a conical portion with a tip having an external thread for inserting the pin inside a bone; said elongated cylindrical stem comprising a first portion with a diameter and a second opposite portion, wherein said second opposite portion of the elongated cylindrical stem has a flattened surface which lies along a reference plane parallel to the longitudinal axis; said conical portion with the tip having an overall length, measured along the longitudinal axis, equal to the diameter of the stem ±20% of said diameter; said conical portion comprises a tip and a threaded portion; said tip comprising a centring zone which extends longitudinally over a length equal to 6-8% of the diameter of the stem; said conical portion further comprising two base cones having two different angles of conicity, a first base cone in a distal position with respect to the elongated cylindrical stem of the monocortical pin and a second base cone in a proximal position with respect to the elongated cylindrical stem of the monocortical pin; said first base cone having an angle of conicity of 13°; said second base cone having an angle of conicity of 26°.

2. The monocortical pin according to claim 1, wherein said conical portion has a connecting zone (39) at the point where the angle of conicity of the base cone changes.

3. The monocortical pin according to claim 1, wherein said conical portion comprises a cutting face which extends longitudinally over a length equal to about 40% of the diameter of the stem.

4. The monocortical pin according to claim 1, wherein the external thread of the threaded portion has a first crest along a plane containing the longitudinal axis and rotated through an angle of 50° with respect to the reference plane.

5. The monocortical pin according to claim 4, wherein the tip of the conical portion comprises inclined surfaces, said inclined surfaces having an angular position with respect to the first crest of the external thread defined with a tolerance of +/−1°.

6. The monocortical pin according to claim 5, wherein the inclined surfaces of the tip of the conical portion determine the angles of conicity of said tip; said angles of conicity being different depending on the angular position of the monocortical pin.

7. The monocortical pin according to claim 1, wherein the tip of the conical portion has an angle of conicity of 60°+/−2° when sectioned along a plane containing the longitudinal axis and perpendicular with respect to the reference plane and wherein said tip of the conical portion has an angle of conicity of 86°+/−2° when sectioned along a plane containing the longitudinal axis and inclined by 120° with respect to the reference plane.

8. The monocortical pin according to claim 1, wherein the external thread of the conical portion has a proximal flank and a distal flank with respect to the elongated cylindrical stem of the monocortical pin, said proximal flank and distal flank having a respective different inclination with respect to a centre plane situated perpendicular to the lateral surface (43) of the respective base cone.

9. The monocortical pin according to claim 8, wherein said distal flank is inclined by 19° and said proximal flank is inclined by 15°.

* * * * *